United States Patent [19]
Kitahara et al.

[11] Patent Number: 4,731,333
[45] Date of Patent: Mar. 15, 1988

[54] METHOD FOR DETECTING GASEOUS HYDRIDES

[75] Inventors: Koichi Kitahara; Takashi Shimada, both of Kanagawa, Japan

[73] Assignee: Japan Pionics., Ltd., Tokyo, Japan

[21] Appl. No.: 878,537

[22] Filed: Jun. 25, 1986

[30] Foreign Application Priority Data

Jun. 25, 1985 [JP] Japan ............................... 60-138751

[51] Int. Cl.$^4$ ............................................ G01N 21/78
[52] U.S. Cl. ........................................ 436/72; 436/80;
 436/103; 436/124; 436/133; 436/164; 436/167;
 436/169; 436/182; 436/183; 436/902; 436/904
[58] Field of Search ................... 436/72, 80, 103, 124,
 436/133, 164, 167, 169, 170, 182, 183, 902, 904

[56] References Cited

U.S. PATENT DOCUMENTS

| | | | |
|---|---|---|---|
| 1,321,062 | 11/1919 | Lamb et al. | 436/103 X |
| 2,805,132 | 9/1957 | Kuhns | 436/182 |
| 2,848,307 | 8/1958 | Hill | 436/182 |
| 3,112,998 | 12/1963 | Grosskopf | 436/103 X |
| 4,176,137 | 11/1979 | Platz et al. | 502/244 X |
| 4,254,214 | 3/1981 | Takeda et al. | 430/523 X |
| 4,384,146 | 5/1983 | Tang | 568/861 |
| 4,419,273 | 12/1983 | Santilli et al. | 502/84 X |
| 4,447,543 | 5/1984 | Harada et al. | 436/72 |
| 4,532,120 | 7/1985 | Smith et al. | 436/103 X |

FOREIGN PATENT DOCUMENTS 0963949 2/1983 U.S.S.R. ............................... 436/103

OTHER PUBLICATIONS

Nelson et al., Anal. Chem., vol. 29, No. 11, pp. 1665–1666, 1957.

Primary Examiner—Barry S. Richman
Assistant Examiner—Robert J. Hill, Jr.
Attorney, Agent, or Firm—Sughrue, Mion, Zinn, Macpeak, and Seas

[57] ABSTRACT

A solid detecting reagent for gaseous hydrides and a gaseous hydride detecting method are disclosed, said reagent comprising a basic copper carbonate as a color changing component and undergoing color change upon contact with at least one gaseous hydride selected from the group consisting of arsine, phosphine, diborane, hydrogen selenide, germane, monosilane, disilane and dichlorosilane. The reagent is applicable to all of these gaseous hydrides and, upon contact therewith, rapidly changes from an initial blue color to a black color, said black color standing for a long period of time.

8 Claims, No Drawings

METHOD FOR DETECTING GASEOUS HYDRIDES

FIELD OF THE INVENTION

This invention relates to a detecting reagent for gaseous hydrides and a method of detecting gaseous hydrides using the same. More particularly, it relates to a detecting reagent for detecting arsine, phosphine, diborane, hydrogen selenide, germane, monosilane, disilane and dichlorosilane used in the production of semiconductors, etc., and a method of detecting these gaseous hydrides using the detecting agent.

BACKGROUND OF THE INVENTION

With recent developments of the semiconductor industry, kinds and quantities of gases used therefor have been markedly increasing. Of these gases, gaseous hydrides are not only highly toxic but also flammable and, therefore, should be handled with sufficient care.

Therefore, on handling these gases, detection in a working atmosphere should constantly be carried out. In cases where these gases leak out by any possiblity, a proper and well-timed measure should be taken to notify the workers of the leakage.

On the other hand, since exhausted gases discharged from the production step of semiconductors contain these gaseous hydrides, it is cleaned by means of a waste gas purifying device, etc., before discharge to an open atmosphere. In this case, also, it is necessary to confirm removal of these gaseous hydrides before the waste gas is discharged.

Known methods of detecting the aforesaid gaseous hydrides utilize color change of a detecting reagent packed in a glass tube which is caused by reaction between the detecting reagent and a gas to be detected. Conventionally known detecting reagents include, for example, mercury (II) or a complex salt thereof or a mixture thereof with a ferric salt or a cupric salt adsorbed on silica gel particles for detecting phosphine; and chemicals consisting of gold adsorbed on silica gel particles for detecting phosphine, arsine or diborane.

However, each of these known detecting reagents is capable of detecting only limited kinds of gases so that gases detectable by one kind of a detector tube are so limited. Moreover, after these detecting reagents once undergo color change, they return to their original color with the passage of time. This incurs the possibility of passing over the color change in cases when gaseous hydrides exist only temporarily. Further, detecting reagents that are of practical utility in detection of monosilane and disilane have not yet been developed. Under these circumstances, there is no means for detection this is commonly applicable to all of the gaseous hydrides used in the production of semiconductors, etc., with high sensitivity.

In addition to the above-described detector tubes, a detecting method for gaseous hydrides by means of a detecting alarm based on several ideas is also known. However, such an alarm is also limited in kind of gases to be detected and, in addition, is complicated in measurement principle and structure.

Accordingly, it has been highly desirable to develop a detecting reagent which can be applied to various kinds of gaseous hydrides and suffers less color disappearance after color change.

SUMMARY OF THE INVENTION

An object of this invention is to provide a detecting reagent capable of detecting substantially all of the gaseous hydrides used in the production of semiconductors, etc., with high sensitivity.

Another object of this invention is to provide a detecting reagent which undergoes color change upon contact with the above-described gaseous hydrides and does not return to its original color, thus eliminating the possibiltiy of passing over the existence of the gaseous hydrides.

A further object of this invention is to provide a detecting method for the gaseous hydrides, which can be applied to wider uses, for example, to detection of breakthrough of gaseous hydrides by packing a detecting reagent in an outlet part of a waste gas purifying equipment, e.g., a gas adsorption cylinder, or to detection of gas leakage in a working atmosphere.

As a result of extensive investigations to solve the above-described problems associated with the conventional techniques, it has now been found that basic copper carbonates are very excellent as a color changing component to be used for detection of gaseous hydrides used in the production step of semiconductors, etc. The present invention has thus been completed based on this finding.

That is, the present invention relates to a solid detecting reagent for detecting gaseous hydrides, which comprises a basic copper carbonate as a color changing component and which undergoes color change upon contact with at least one gaseous hydride selected from the group consisting of arsine, phosphine, diborane, hydrogen selenide, germane, monosilane, disilane and dichlorosilane.

The detecting reagent according to the present invention can be commonly used for detecting gaseous hydride-containing gases, such as hydrogen gas, argon gas, helium gas, air, etc. Upon contact with these gases, the detecting reagent of the invention changes its color from blue to black with high sensitivity, and the color thus changed stands for a long period of time. The black color of the detecting reagent once produced by color change may gradually fade with the passage of time depending on the kinds or concentrations of gases but never returns to the initial blue color.

DETAILED DESCRIPTION OF THE INVENTION

The basic copper carbonates which are used as a color changing component of the detecting reagent of the invention usually have a blue to green color, with those having blue shades being particularly preferred.

The basic copper carbonates can be obtained by, for example, reacting copper sulfate, copper nitrate, copper halides or various copper salts of organic acids with sodium carbonate, potassium carbonate, sodium bicarbonate, potassium bicarbonate, etc., collecting the precipitate formed, washing the precipitate with water and drying it at a temperature of from about 100° to about 200° C. Commercially available basic copper carbonates or natural blue azurite grinds may also be employed.

In the present invention, the basic copper carbonate itself, which is a color changing component, may be used as a solid detecting reagent as is in the form of powder or after being molded into pellets, or it may be supported on a carrier, preferably a porous carrier, to form a solid detecting reagent. Solid detecting reagents in the molded form or supported form are preferred. In particular, those supported on a porous carrier are more preferred.

The carrier to be used can be selected from various materials and includes carriers generally employed for catalysts, such as silica gel, silica alumina, alumina, and the like. Of these, silica alumina and alumina are preferred. Further, those having a specific surface area of not more than 50 $m^2/g$ are preferred. In general, carriers having light colors are used, and white or colorless carriers are preferably used. The color changing component can be supported on these carriers by impregnating a porous carrier with the basic copper carbonate or, more easily, by scattering the basic copper carbonate on the surface of carrier. The amount of the basic copper carbonate to be supported usually ranges from 1 to 30% by weight, and preferably from 1 to 10% by weight, based on the carrier.

In the case of molding the basic copper carbonate in pellets or similar forms, molding can be carried out either by a dry process or a wet process. The shape of molded articles is not particularly restricted and includes a sphere, a column, etc. The molded articles may be ground to an appropriate size.

The solid detecting reagent in accordance with the present invention changes in color into black when contacted with various gaseous hydrides, and this color change can easily be recognized from its external appearance. The black color after the color change can stand for an extended period of time even when allowed to stand in a nitrogen or hydrogen atmosphere or in air.

Concentrations of gaseous hydrides detectable with the solid detecting reagents of the present invention are usually 0.1 ppm or higher as for arsine, phosphine, diborane, germane, and hydrogen selenide; and 10 ppm or higher as for monosilane, disilane and dichlorosilane. However, gaseous hydrides having a concentration below the above lower limit can also be detected since color change may occur after the gaseous hydrides are contacted with the detecting reagents for a prolonged time even at such low concentrations. The flow rate of the gas to be contacted with the detecting reagent usually ranges from 0.01 to 100 cm/sec in terms of linear velocity. The gas at the time of contact usually has a temperature of from $-20°$ to $100°$ C. and a pressure of from 0.001 to 20 $kg/cm^2$ abs.

The detecting reagents according to the present invention are solid and are usually packed in a transparent container (usually, a cylinder or a tube) upon use. Existence of gaseous hydrides in an atmosphere can be noted from the color change of the detecting reagent. The detecting reagents of the present invention may be used as packed in a detector tube, or in a simpler and easier embodiment, it is packed in a transparent container (usually a tube) made of glass, plastics, etc., through which gases to be detected are passed. This embodiment is applied to detection of gaseous hydrides in a working atmosphere. In case of detecting gaseous hydrides in waste gas discharged from the production of semiconductors, etc., the detecting reagent is usually combined with a waste gas removal process. In this case, the detecting reagent is placed behind a layer of a gaseous hydride-removing agent of a gas removal cylinder or between a plurality of layers or packed in a detector tube, which is connected behind a gas removal cylinder.

The detecting reagents in accordance with the present invention bring about the following excellent effects and are very useful in industry.

(1) They can be commonly applied to substantially all of gaseous hydrides used in the production of semiconductors, etc., with high sensitivity.

(2) Since the reagents once having undergone color change upon contact with gaseous hydrides do not return to their initial color, the color change would not be overlooked.

(3) They can be used for a wide variety of utilities, for example, for detecting breakthrough of gaseous hydrides by packing them in an outlet part of a waste gas purifying equipment, e.g., a gas adsorption cylinder, or for detecting gas leakage in a working atmosphere.

This invention will now be illustrated in greater detail with reference to the following examples, but it should be understood that they are intended to limit the present invention. In these examples, all the percents are by weight unless otherwise indicated.

EXAMPLES 1 to 12

A 20% aqueous solution of sodium carbonate was added dropwise to a 20% aqueous solution of copper sulfate while stirring in an agitator to form a basic copper carbonate precipitate. The precipitate was collected by filtration, washed with water and dried at $100°$ C. to obtain a powder of basic copper carbonate having a blue color.

The powder was scattered on α-alumina having a specific surface area of 0.005 to 0.040 $m^2/g$ (SA-5218, produced by Norton Co.) to prepare a detecting reagent comprising about 4% of the basic copper carbonate.

About 5 g of the detecting reagent was charged in a rigid polyvinyl chloride container having an inner diameter of 25 mm and a height of 100 mm, and nitrogen gas, hydrogen gas or air containing gaseous hydrides was passed therethrough at a rate of 5 l/min to observe color change of the detecting reagent. In each case, the initial blue reagent rapidly turned black.

After the color change, the reagent was allowed to stand in nitrogen gas, hydrogen gas or air for 10 hours to observe its color. The black color of the reagent underwent substantially no change.

These results are shown in Table 1 below.

COMPARATIVE EXAMPLES 1 AND 2

The same test as described in Example 1 was repeated but using a commercially available arsine detecting reagent (Detector Tube No. 19L, produced by GAS TECH Co.) (Comparative Example 1) or phosphine detecting reagent (Detector Tube No. 121SD, produced by Komyo Rikagaku Co). In each case, the reagent changed from the initial yellow color to a purple color, but completely returned to its original yellow color when allowed to stand in air for 2 hours. These results are also shown in Table 1.

TABLE 1

| Example No. | Gaseous Hydride Kind | Concentration (ppm) | Carrier Gas | Color Change | Color Change after 10 Hr Standing In $N_2$ | In $H_2$ | In Air |
|---|---|---|---|---|---|---|---|
| Example 1 | $AsH_3$ | 0.1 | $N_2$ | Blue→Black | No Change | — | No Change |
| Example 2 | $AsH_3$ | 0.1 | $H_2$ | Blue→Black | — | No Change | No Change |
| Example 3 | $AsH_3$ | 0.1 | Air | Blue→Black | — | — | No Change |
| Example 4 | $PH_3$ | 0.1 | $N_2$ | Blue→Black | No Change | — | No Change |
| Example 5 | $PH_3$ | 0.1 | $H_2$ | Blue→Black | — | No Change | No Change |
| Example 6 | $PH_3$ | 0.1 | Air | Blue→Black | — | — | No Change |
| Example 7 | $GeH_4$ | 0.1 | $N_2$ | Blue→Black | No Change | — | No Change |
| Example 8 | $H_2Se$ | 0.1 | $N_2$ | Blue→Black | No Change | — | No Change |
| Example 9 | $B_2H_6$ | 0.1 | $N_2$ | Blue→Black | No Change | — | No Change |
| Example 10 | $SiH_4$ | 10 | $N_2$ | Blue→Black | No Change | — | No Change |
| Example 11 | $Si_2H_6$ | 10 | $N_2$ | Blue→Black | No Change | — | No Change |
| Example 12 | $SiH_2Cl_2$ | 10 | $N_2$ | Blue→Black | No Change | — | No Change |
| Comparative Example 1 | $AsH_3$ | 5 | $N_2$ | Yellow→Purple | — | — | Purple*→Yellow |
| Comparative Example 2 | $PH_3$ | 5 | $N_2$ | Yellow→Purple | — | — | Purple*→Yellow |

Note:
*Color change after 2 hour standing.

EXAMPLE 13

An MOCVD (metal organic chemical vapor deposition) device in the production for Ga.As compound semiconductors from trimethyl gallium and arsine discharged the waste gas comprising hydrogen and 2% of arsine at a rate of 5 l/min.

A waste gas removing agent comprising a mixture of copper oxide and zinc oxide was charged in a transparent quartz cylinder having an inner diameter of 55 mm and a height of 500 mm to a height of 300 mm, and the solid detecting agent as prepared in Example 1 was charged in the cylinder downstream of the removing agent layer to an additional height of 30 mm to form a waste gas removal cylinder.

The above-described arsine-containing hydrogen gas discharged from the MOCVD device was passed through the removal cylinder to thereby remove arsine while observing color change of the detecting reagent. As a result, the initially blue-colored detecting reagent began to change its color to black after 980 minutes from the start of waste gas passage, indicating that the removing agent layer was broken through and arsine reached the detecting reagent layer. Two minutes later from the beginning of the color change, the whole detecting agent layer changed to black. It was not until that time that a commerically available detecting tube (Detector Tube No. 19L, produced by GAS TECH Co.) could detect 0.1 ppm of arsine in the waste gas at the outlet of the removal cylinder.

While the invention has been described in detail and with reference to specific embodiments thereof, it will be apparent to one skilled in the art that various changes and modifications can be made therein without departing from the spirit and scope thereof.

What is claimed is:

1. A method of detecting gaseous hydrides comprising contacting a solid detecting reagent comprising a basic copper carbonate as a color changing component with a waste gas discharged from a process of production of semiconductors containing at least one gaseous hydride selected from the group consisting of arsine, phosphine, diborane, hydrogen selenide, germane, monosilane, disilane and dichlorosilane and observing a change in color of the detecting reagent.

2. A method as in claim 1, wherein the gas containing at least one gaseous hydride is nitrogen, hydrogen, argon, helium or air or a mixture thereof.

3. A method as in claim 1, wherein said waste gas is passed through a layer for removing gaseous hydrides so as to have reduced concentrations of gaseous hydrides prior to the contact with said solid detecting reagent.

4. A method as in claim 1, wherein said detecting reagent is charged in a cylinder or tube, through which said gas containing at least one gaseous hydride is passed.

5. A method as in claim 4, wherein said cylinder or tube is transparent.

6. A method as in claim 1, wherein said basic copper carbonate is supported on a porous carrier.

7. A method as in claim 6, wherein said porous carrier is silica, silica alumina or alumina.

8. A method as in claim 6, wherein said porous carrier has a specific surface area of not more than 50 $m^2/g$.

* * * * *